(12) United States Patent
Capote et al.

(10) Patent No.: US 11,701,097 B2
(45) Date of Patent: *Jul. 18, 2023

(54) SURGICAL RETRACTOR AND METHOD OF USE

(71) Applicant: WARSAW ORTHOPEDIC INC., Warsaw, IN (US)

(72) Inventors: Cristian A. Capote, Memphis, TN (US); Anthony J. Melkent, Memphis, TN (US); Stanley T. Palmatier, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 264 days.

This patent is subject to a terminal disclaimer.

(21) Appl. No.: 17/064,809

(22) Filed: Oct. 7, 2020

(65) Prior Publication Data

US 2021/0077085 A1 Mar. 18, 2021

Related U.S. Application Data

(63) Continuation of application No. 13/550,864, filed on Jul. 17, 2012, now Pat. No. 10,835,228.

(51) Int. Cl.
*A61B 17/02* (2006.01)
*A61B 17/00* (2006.01)

(52) U.S. Cl.
CPC .............. *A61B 17/0206* (2013.01); *A61B 2017/00407* (2013.01); *A61B 2017/0256* (2013.01)

(58) Field of Classification Search
CPC ...... A61B 17/0206; A61B 2017/00407; A61B 2017/0256

See application file for complete search history.

(56) References Cited

U.S. PATENT DOCUMENTS

| 3,965,890 A | 6/1976 | Gauthier |
| 4,116,232 A | 9/1978 | Rabban |
| 4,263,899 A | 4/1981 | Burgin |
| 4,337,762 A | 7/1982 | Gauthier |
| 4,421,107 A | 12/1983 | Estes et al. |
| 4,421,108 A | 12/1983 | Cabrera et al. |
| 4,467,791 A | 8/1984 | Cabrera et al. |
| 4,617,916 A | 10/1986 | Levahn et al. |
| 4,627,421 A | 12/1986 | Symbas et al. |
| 4,718,151 A | 1/1988 | Levahn et al. |
| 4,747,395 A | 5/1988 | Brief |
| 4,813,401 A | 3/1989 | Grieshaber |
| 4,949,707 A | 8/1990 | Levahn et al. |
| 5,027,793 A | 7/1991 | Engelhardt et al. |
| 5,052,374 A | 10/1991 | Manuel |

(Continued)

*Primary Examiner* — Samuel S Hanna
(74) *Attorney, Agent, or Firm* — Sorell, Lenna & Schmidt, LLP

(57) ABSTRACT

A surgical retractor includes a first member defining a longitudinal axis. The first member includes a blade disposed in spaced apart relation relative to the longitudinal axis and a grip surface. A second member has a blade disposed in spaced apart relation relative to the longitudinal axis and a grip surface. The grip surfaces are configured to be drawn together along the longitudinal axis such that the blades are engageable with tissue and connected with the grip surfaces such that the grip surfaces provide a tactile feedback of the tissue engagement. Systems and methods of use are disclosed.

20 Claims, 7 Drawing Sheets

(56) References Cited

U.S. PATENT DOCUMENTS

| | | |
|---|---|---|
| 5,080,088 A | 1/1992 | Levahn |
| 5,167,392 A | 12/1992 | Henricksen |
| 5,253,638 A | 10/1993 | Tamburrino et al. |
| 5,299,563 A | 4/1994 | Seton |
| 5,375,481 A | 12/1994 | Cabrera et al. |
| 5,381,787 A | 1/1995 | Bullard |
| 5,409,496 A | 4/1995 | Rowden et al. |
| 5,503,617 A | 4/1996 | Jako |
| 5,520,608 A | 5/1996 | Cabrera et al. |
| 5,520,610 A | 5/1996 | Giglio et al. |
| 5,520,698 A | 5/1996 | Koh |
| 5,540,700 A | 7/1996 | Rowden et al. |
| 5,558,621 A | 9/1996 | Heil |
| 5,643,285 A | 7/1997 | Rowden et al. |
| 5,728,046 A | 3/1998 | Mayer et al. |
| 5,740,791 A | 4/1998 | Aves |
| 5,741,210 A | 4/1998 | Dobrovolny |
| 5,782,753 A | 7/1998 | Defonzo et al. |
| 5,876,333 A | 3/1999 | Bigliani et al. |
| 5,947,896 A | 9/1999 | Sherts et al. |
| D415,274 S | 10/1999 | Koros et al. |
| 5,964,697 A | 10/1999 | Fowler, Jr. |
| 5,964,698 A | 10/1999 | Fowler |
| 5,984,865 A | 11/1999 | Farley et al. |
| 6,017,306 A | 1/2000 | Bigliani et al. |
| D420,130 S | 2/2000 | Nicholas et al. |
| 6,042,541 A | 3/2000 | Dobrovolny et al. |
| 6,042,542 A | 3/2000 | Koros et al. |
| 6,102,853 A | 8/2000 | Scirica et al. |
| 6,102,854 A | 8/2000 | Cartier et al. |
| 6,117,072 A | 9/2000 | Fowler, Jr. |
| 6,190,312 B1 | 2/2001 | Fowler, Jr. |
| 6,193,651 B1 | 2/2001 | Defonzo |
| D438,966 S | 3/2001 | Koros et al. |
| 6,200,263 B1 | 3/2001 | Person |
| 6,241,659 B1 | 6/2001 | Bookwalter et al. |
| 6,254,532 B1 | 7/2001 | Paolitto et al. |
| 6,264,605 B1 | 7/2001 | Scirica et al. |
| 6,306,085 B1 | 10/2001 | Farascioni |
| 6,468,207 B1 | 10/2002 | Fowler, Jr. |
| 6,530,883 B2 | 3/2003 | Bookwalter et al. |
| 6,537,212 B2 | 3/2003 | Sherts et al. |
| 6,565,508 B2 | 5/2003 | Scirica et al. |
| 6,610,009 B2 | 8/2003 | Person |
| 6,648,818 B2 | 11/2003 | Cartier et al. |
| 6,659,945 B2 | 12/2003 | Ball et al. |
| 6,689,053 B1 | 2/2004 | Shaw et al. |
| 6,709,389 B2 | 3/2004 | Farascioni |
| 6,740,029 B2 | 5/2004 | Rogers et al. |
| 6,860,850 B2 | 3/2005 | Phillips et al. |
| 6,958,038 B2 | 10/2005 | Feng et al. |
| 7,014,608 B2 | 3/2006 | Larson et al. |
| 7,014,609 B2 | 3/2006 | Cartier et al. |
| 7,033,361 B2 | 4/2006 | Collazo |
| 7,097,616 B2 | 8/2006 | Bjork et al. |
| 7,125,379 B2 | 10/2006 | Bjork et al. |
| 7,137,949 B2 | 11/2006 | Scirica et al. |
| 7,144,368 B2 | 12/2006 | Larson et al. |
| 7,144,393 B2 | 12/2006 | Dipoto et al. |
| 7,179,225 B2 | 2/2007 | Shluzas et al. |
| 7,226,451 B2 | 6/2007 | Shluzas et al. |
| 7,294,104 B2 | 11/2007 | Person |
| 7,611,460 B2 | 11/2009 | Dobrovolny |
| 7,645,232 B2 | 1/2010 | Shluzas |
| 7,654,954 B1 | 2/2010 | Phillips et al. |
| 7,691,120 B2 | 4/2010 | Shluzas et al. |
| 7,736,305 B2 | 6/2010 | Dipoto |
| 7,744,530 B2 | 6/2010 | Person |
| 7,766,930 B2 | 8/2010 | Dipoto et al. |
| 7,811,230 B2 | 10/2010 | Hsueh et al. |
| 7,824,332 B2 | 11/2010 | Fakhrai |
| 7,976,464 B2 | 7/2011 | Shluzas et al. |
| 7,985,218 B2 | 7/2011 | Dipoto et al. |
| 8,007,492 B2 | 8/2011 | Dipoto et al. |
| 8,062,217 B2 | 11/2011 | Boucher et al. |
| 8,114,020 B2 | 2/2012 | Fricke et al. |
| 8,162,827 B2 | 4/2012 | Abdelgany et al. |
| 2005/0234304 A1* | 10/2005 | Dewey ............... A61B 17/3439 600/210 |
| 2009/0036746 A1* | 2/2009 | Blackwell .......... A61B 17/0206 600/219 |
| 2010/0317928 A1* | 12/2010 | Subramaniam ........ A61B 90/30 600/245 |
| 2013/0046147 A1* | 2/2013 | Nichter ............... A61B 17/0206 600/228 |
| 2013/0096387 A1* | 4/2013 | DeRidder .......... A61B 17/0206 600/214 |

\* cited by examiner

SURGICAL RETRACTOR AND METHOD OF USE

CROSS-REFERENCE TO RELATED APPLICATIONS

This application is a continuation of U.S. patent application Ser. No. 13/550,864, filed on Jul. 17, 2012, which is hereby incorporated by reference herein, in its entirety.

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

SUMMARY

Accordingly, a surgical system and method are provided for accessing a surgical site, which may include, for example, a portion of a spine to facilitate treatment thereof. It is contemplated that the surgical system and method may be employed for exposing and providing a surgical pathway to a surgical site.

In one embodiment, in accordance with the principles of the present disclosure, a surgical retractor is provided. The retractor includes a first member defining a longitudinal axis. The first member includes a blade disposed in spaced apart relation relative to the longitudinal axis and a grip surface. A second member has a blade disposed in spaced apart relation relative to the longitudinal axis and a grip surface. The grip surfaces are configured to be drawn together along the longitudinal axis such that the blades are engageable with tissue and connected with the grip surfaces such that the grip surfaces provide a tactile feedback of the tissue engagement.

In one embodiment, a method of treating a spine is provided. The method comprises the steps of providing a surgical retractor comprising a first member defining a longitudinal axis and including a blade disposed in spaced apart relation relative to the longitudinal axis and a grip surface and a second member including a blade disposed in spaced apart relation relative to the longitudinal axis and a grip surface, wherein the grip surface of the second member includes a first portion and a second portion spaced apart from the first portion; disposing a first finger into engagement with the first portion and a second finger into engagement with the second portion; disposing a third finger into engagement with the grip surface of the first member; and compressing the grip surfaces to draw the grip surfaces together such that the blades space apart to engage tissue and the grip surfaces provide tactile feedback to the fingers of the tissue engagement.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
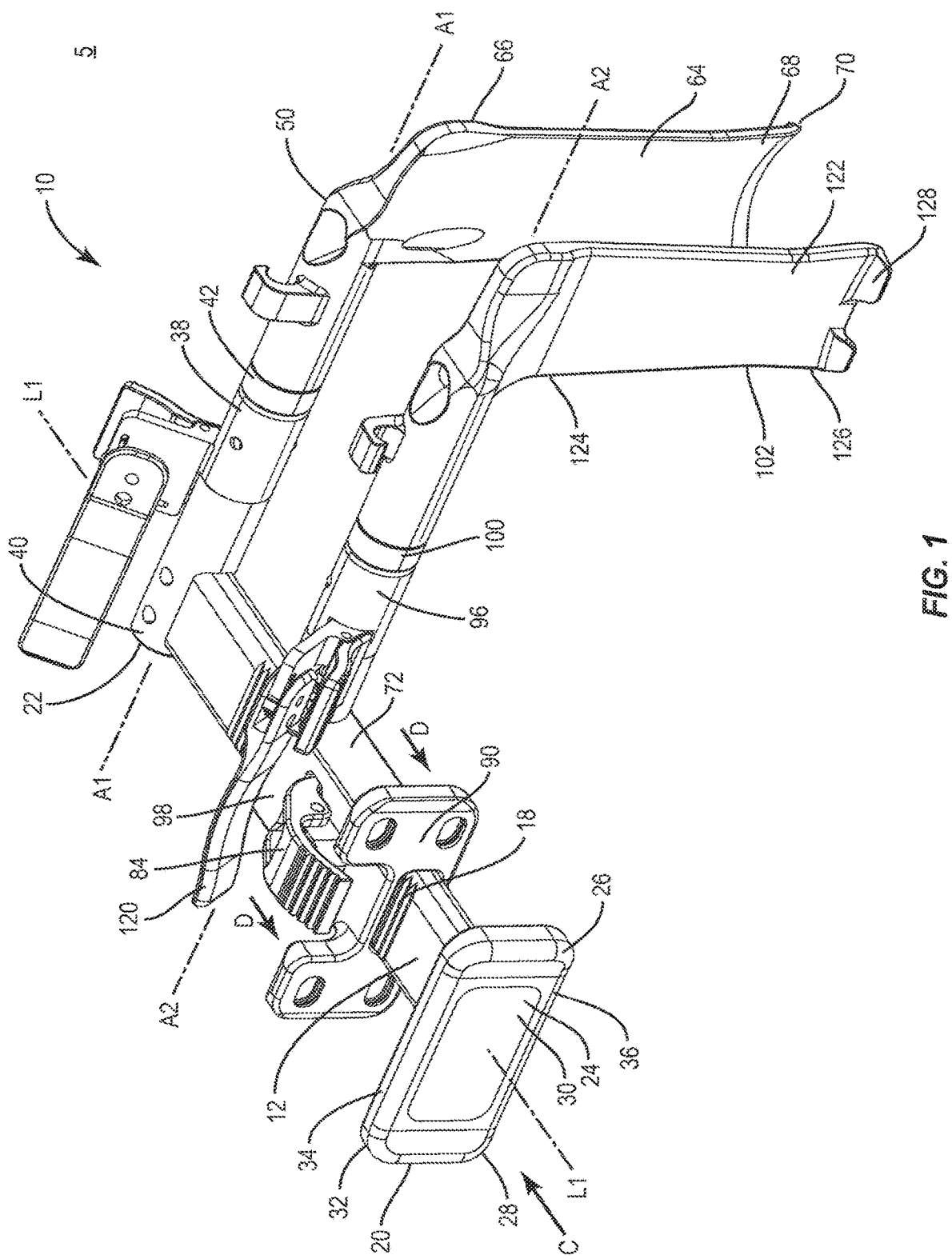
FIG. 1 is a perspective view of one embodiment of components of a system in accordance with the principles of the present disclosure.
Figure 2:
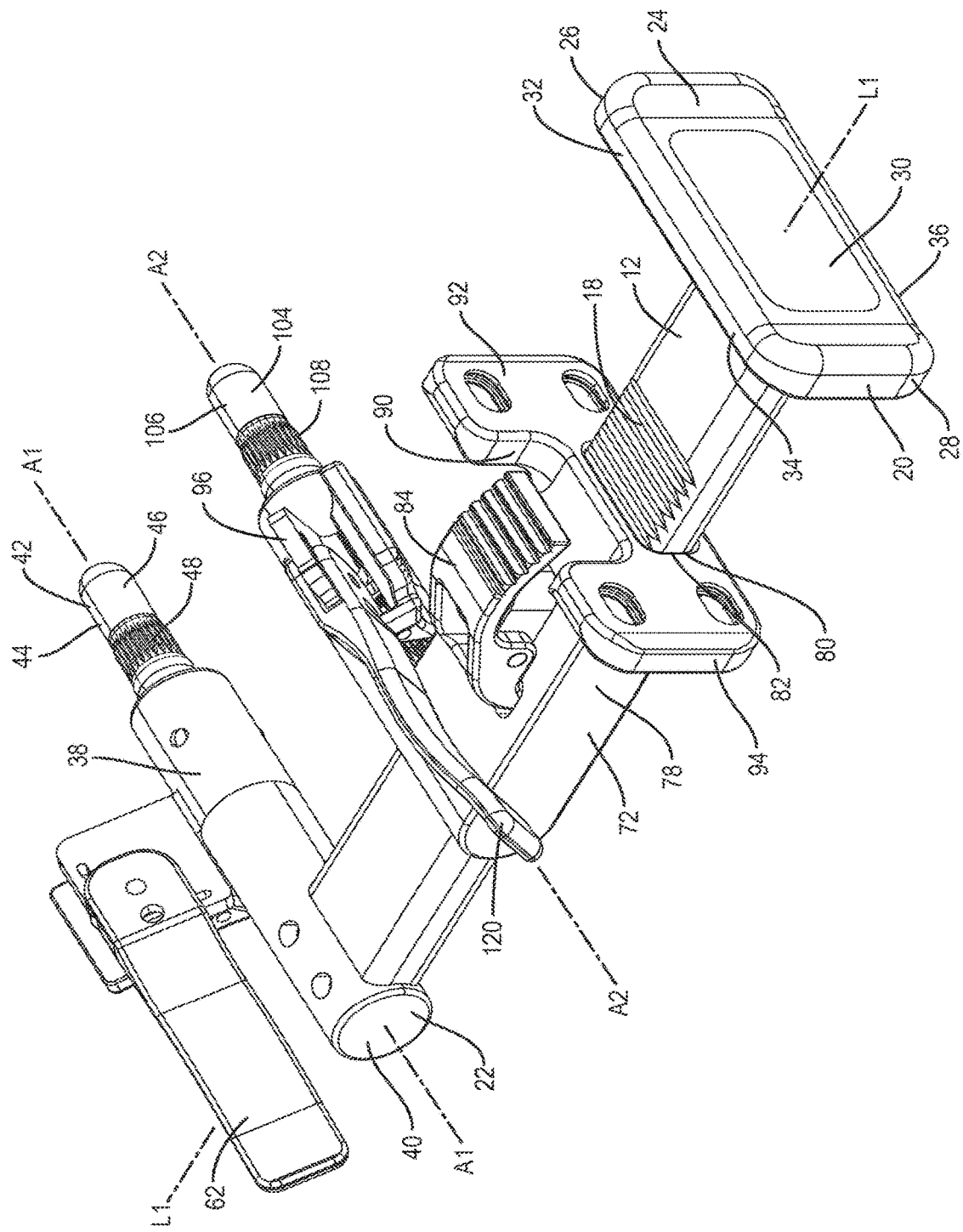
FIG. 2 is a perspective view of components of the system shown in FIG. 1.

The exemplary embodiments of the surgical system and related methods of use disclosed are discussed in terms of medical devices for the treatment of musculoskeletal disorders and more particularly, in terms of a surgical system for accessing a spine to facilitate treatment thereof and a method for treating a spine. One or all of the system components may be reusable or disposable. The surgical system may be configured as a kit with multiple sized and configured components.

In one embodiment, the system includes a surgical retractor for tissue retraction from a midline approach for surgery of a spine, including minimally invasive applications. In one embodiment, the surgical retractor includes one or a plurality of blades to create access through soft tissue. In one embodiment, the surgical retractor includes a blade rotation mechanism for creating access to a surgical site.

In one embodiment, the surgical retractor includes a shaft, such as, for example, a hand actuated locking rack, which provides translation of the rack to a selected position. In one embodiment, a first surface includes protrusions on a translating arm of the surgical retractor having finger grips for a practitioner and a second surface disposed on a stationary arm that allows for pressure applied by a practitioner's palm. It is contemplated that the practitioner moves fingers in an axial direction towards the practitioner, in a gripping motion, to actuate the rack. This motion ergonomically conforms to natural human hand strength and provides a 1:1 input to output force ratio such that a tactile feedback including the force the practitioner feels in the palm is a direct output force applied to the tissue during retraction of the tissue. This configuration provides an accurate tactile feedback.

In one embodiment, the surgical retractor has a blade interface, which includes locking tips to provide rotation in 7.5 degree increments. In one embodiment, the surgical retractor includes a latching or toothed rack mechanism that includes wings, which can be positioned for locking blades in an initial position and unlocking the blades for rotation in situ.

In one embodiment, the surgical retractor includes a top mounted rack with an increased cross section. In one embodiment, the surgical retractor includes a top mounted, low-profile latch with a locking feature. The latch facilitates a range of 30 degrees of rotation with an indexing feature that includes rotation of 7.5 degree increments. In one embodiment, the surgical retractor includes a main shaft with a blade paddle interface having an increased surface area and ball detent retention surface. In one embodiment, the surgical retractor includes ergonomic gripping surfaces for one-handed operation.

In one embodiment, the surgical retractor includes an opposing grip configuration distraction mechanism. The configuration enables a practitioner to open blades by pushing the rack forward with a thumb while applying counter pressure with an index/middle finger. In one embodiment, the practitioner can employ two hands.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a surgical system 5 including a retractor for accessing a spine to facilitate treatment thereof in accordance with the principles of the present disclosure.

The components of surgical system 5 can be fabricated from biologically acceptable materials suitable for medical applications, including metals, synthetic polymers, ceramics and/or their composites, depending on the particular application and/or preference of a medical practitioner. For example, the components of surgical system 5, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, composites of PEEK and calcium based ceramics, and composites of PEEK with resorbable polymers. Various components of surgical system 5 may have material composites, including the above materials, to achieve various desired characteristics such as strength, rigidity, elasticity, compliance, biomechanical performance, durability and radiolucency or imaging preference. The components of surgical system 5, individually or collectively, may also be fabricated from a heterogeneous material such as a combination of two or more of the above-described materials. The components of surgical system 5 may be monolithically formed, integrally connected or include fastening elements and/or instruments, as described herein.

Surgical system 5, is employed, for example, with minimally invasive, mini-open and/or open procedures for supporting tissue and/or anatomical structures to expose tissue and/or anatomical structures to create a surgical pathway and provide access to a surgical site, which includes, for example, a spine to facilitate treatment.

Surgical system 5 includes a retractor assembly 10 having a first member, such as, for example, a shaft 12. Shaft 12 defines a longitudinal axis L1 and an outer surface 14. Outer surface 14 includes a rack 16. Rack 16 includes a plurality of teeth 18 configured to engage a second member, as described, for selective positioning of retractor blades. Rack 16 extends between a first end and a second end in a configuration to provide a range of spacing and/or distraction of retractor blades for selective spacing of tissue at a surgical site. Shaft 12 includes an increased cross section relative to its height such that rack 16 has a wide surface area relative to the height. It is contemplated that all or only a portion of outer surface 14 includes various surface configurations, such as, for example, smooth, rough, mesh, porous, semi-porous, dimpled and/or textured according to the requirements of a particular application. In one embodiment, retractor assembly 10 may be employed with a free hand surgical technique or with a base connected to a frame (not shown).

Shaft 12 extends between a first end 20 and a second end 22. End 20 includes a grip surface 24. Grip surface 24 includes a first portion 26 and a second portion 28. Portion 26 extends laterally outward in a first direction from outer surface 14 and transverse to axis L1. Portion 28 extends laterally outward in a second direction, opposite to the first direction of portion 26, and transverse to axis L1. It is envisioned that portion 26 and/or portion 28 may extend from outer surface 14 in various orientations, relative to axis L1, such as, for example, co-axial, angularly offset, offset and/or staggered relative to axis L1. It is contemplated that portions 26, 28 are monolithically formed with shaft 12. It is contemplated that portions 26, 28 are separate elements attached to shaft 12. It is contemplated that portions 26, 28 can be moveably connected to shaft 12.

Portions 26, 28 define a substantially planar surface 30 that is configured for engagement with the hand of a practitioner, such as, for example, a finger, which can include a thumb. Portions 26, 28 define a continuous outer surface 32 including a substantially planar upper side 34 and a substantially planar lower side 36. It is contemplated that surface 30, side 34 and/or side 36 may include alternative surface configurations, which can be, for example, smooth, rough, mesh, porous, semi-porous, dimpled, arcuate, undulating, pointed and/or textured according to the requirements of a particular application.

End 22 includes a first arm 38 extending along a first axis A1 transverse to axis L1. Arm 38 extends in a perpendicular orientation from shaft 12 along the same plane. It is envisioned that arm 38 may be oriented along axis A1 in alternate configurations, such as, for example, parallel, co-axial, angularly offset, offset and/or staggered relative to axis L1. Arm 38 extends from end 40 to an end 42. End 42 includes an interface configuration that mates with a first blade assembly 50.

End 42 includes a mating shaft 44 that is cylindrical and includes an outer surface 46 having a spline configuration. Outer surface 46 comprises splines 48 disposed in an axial orientation along axis A1. Splines 48 include a plurality of individual spline members that extend in parallel relation about circumferential outer surface 42. The spline configuration provides a mounting and alignment configuration for providing a snap fit between blade assembly 50 and arm 38.

It is envisioned that mating shaft 44 may have alternate cross section configurations, such as, for example, oval, oblong, triangular, rectangular, square, polygonal, irregular, uniform, non-uniform, variable and/or tapered. It is further envisioned that all or only a portion of surface 46 may have alternate surface configurations, such as, for example, rough, threaded for connection with other instruments, arcuate, undulating, porous, semi-porous, dimpled, polished and/or textured according to the requirements of a particular application.

Blade assembly 50 comprises a wall, such as, for example, a barrel 52. Barrel 52 has a circumferential configuration to define an elongated tubular cavity, such as, for example, a bore (not shown) that is disposed along axis A1 and is configured to receive shaft 44. The bore provides a mounting and alignment configuration for mating blade assembly 50 with arm 38.

Barrel 52 includes an inner surface (not shown) that defines a spline configuration, similar to the spline configuration of shaft 44. The inner surface comprises splines disposed in an axial orientation along axis A1. The splines include a plurality of individual spline members that extend in parallel relation about circumferential the inner surface. The spline configuration provides a mounting and alignment configuration, described above, for mating blade assembly 50 with arm 38.

The splines of barrel 52 mate with splines 48 along axis A1 to align and mount blade assembly 50 with arm 38 such that axis A1 intersects axis L1. The mounting and alignment configuration provides facile assembly of blade assembly 50 with arm 38.

Outer surface 46 includes a flange 60 engageable with a lever 62 to facilitate rotation of arm 38. Arm 38 includes a tubular portion that is separate and rotatable relative to shaft 12 via indexing lever 62 such that blade assembly 50 is rotatable about axis A1 and relative to arm 38. Lever 62 has a flip-up configuration and facilitates rotation of arm 38 upon fixation of blade assembly 50 with arm 38, as described. In an upright orientation, lever 62 can be manipulated to rotate arm 38 in the opposing directions shown by arrows A in FIG. 3, which corresponds to rotation of retractor blades, as described below.

Blade assembly 50 includes a paddle and/or blade 64 for indexed rotation about axis A1 relative to shaft 12 in angular increments to engage and/or distract tissue. Lever 62 rotates blade 64 through an angle α and can be indexed in selected angular increments. It is envisioned that angle α may include a range of 0-85 degrees, for example, 30 degrees. It is further envisioned that the angular increments may include a range of 0-15 degrees, for example, 7.5 degrees.

Blade 64 has a substantially flat and/or substantially planar configuration and extends between a proximal end 66 and a distal end 68. Blade 64 includes a plurality of feet 70 disposed adjacent distal end 68. Feet 70 extend outwardly from distal end 68 to engage and/or distract tissue. It is envisioned that the blade(s) may be oriented in alternate configurations, such as, for example, perpendicular, parallel, co-axial, angularly offset, offset and/or staggered relative to axis L1 and/or axis A1. It is contemplated that blade 64 may include alternative surface configurations, which can be, for example, smooth, rough, mesh, porous, semi-porous, dimpled, arcuate, undulating, pointed and/or textured according to the requirements of a particular application. Blade 64 is configured to retract, support and/or space apart tissue from the surgical site.

A second member, such as, for example, a housing 72 extends along axis L1 between a first end 74 and a second end 76. Housing 72 includes an outer surface 78 and an inner surface 80. Inner surface 80 defines an interior cavity 82 configured for movement along shaft 12. In one embodiment, cavity 82 has an oval cross section configuration. It is envisioned that all or only a portion of housing 72 may have alternate cross section configurations, such as, for example, oblong, triangular, square, polygonal, irregular, uniform, non-uniform, offset, staggered, undulating, arcuate, variable and/or tapered.

Housing 72 includes a lock, such as, for example, a latch 84 that is releasably engageable with shaft 12 to selectively distract and/or space apart the retractor blades in a fixed orientation. Latch 84 includes a lever 86 that extends between a first end and a second end. The first end of lever 86 includes a knurled surface to facilitate engagement and/or gripping by a practitioner. The second end of lever 86 includes a protrusion (not shown) configured to engage teeth 18 to fix shaft 12 relative to housing 72. Lever 86 is mounted to housing 72 via a fulcrum and configured for pivotal movement relative to housing 72 and rack 16.

Lever 86 is engageable for pivotable movement between a non-locking configuration such that the protrusion is released from engagement with teeth 18 and shaft 12 is freely slidable relative to housing 72 to selectively position the retractor blades, and a locking configuration such that lever 86 is released from manipulative engagement such that the protrusion engages teeth 18 and shaft 12 is fixed relative to housing 72. In the locking configuration of lever 86, the retractor blades are selectively distracted to space apart tissue according to the requirements of a particular application. Latch 84 includes a spring 88 that resiliently biases lever 86 to the locked configuration.

End 74 of housing 72 includes a second grip surface, such as, for example, finger grips 90. Finger grips 90 include a first portion 92 and a second portion 94. Portion 92 extends laterally from outer surface 78. Portion 92 is configured for engagement with a hand of a practitioner, such as, for example, a first finger. Portion 94 extends laterally from outer surface 78 in an opposite direction from portion 92. Portion 94 is configured for engagement with a hand of a practitioner, such as, for example, a second finger. In one embodiment, a third finger can be utilized with grip surface 24 and/or grip surface 90. In one embodiment, two hands can be utilized such that a thumb is engaged with each side of surface 30 and an index finger is engaged with each side of finger grips 90.

It is contemplated that finger grips 90 include various surface configurations, such as, for example, smooth, rough, mesh, porous, semi-porous, dimpled and/or textured according to the requirements of a particular application. It is envisioned that portion 92 and portion 94 may be oriented in alternate configurations, such as, for example, co-axial, angularly offset, offset and/or staggered relative to axis L1. It is contemplated that finger grips 90 are monolithically formed with housing 72. It is contemplated that finger grips 90 are separate elements attached to housing 72. It is contemplated, that finger grips 90 can be moveably connected to housing 72.

End 76 includes an arm 96 extending along a second axis A2 transverse to axis L1. Arm 96 extends in a perpendicular orientation from housing 72 along the same plane. It is envisioned that arm 96 may be oriented along axis A2 in alternate configurations, such as, for example, parallel, co-axial, angularly offset, offset and/or staggered relative to axis L1. Arm 96 extends from end 98 to an end 100. End 100 includes a blade interface configuration that mates with a second blade assembly 102.

End 100 includes a mating shaft 104 that is cylindrical and includes an outer surface 106 having a spline configuration. Outer surface 106 comprises splines 108 disposed in an axial orientation along axis A2. Splines 108 include a plurality of individual spline members that extend in parallel relation about circumferential outer surface 106. The spline configuration provides a mounting and alignment configuration for mating blade assembly 102 with arm 96.

It is envisioned that shaft 104 may have alternate cross section configurations, such as, for example, oval, oblong, triangular, rectangular, square, polygonal, irregular, uniform, non-uniform, variable and/or tapered. It is further envisioned that all or only a portion of surface 106 may have alternate surface configurations, such as, for example, rough, threaded for connection with other instruments, arcuate, undulating, porous, semi-porous, dimpled, polished and/or textured according to the requirements of a particular application.

Blade assembly 102 comprises a wall, such as, for example, a barrel 110. Barrel 110 has a circumferential configuration to define an elongated tubular cavity, such as, for example, a bore (not shown) that is disposed along axis A2 and is configured to receive shaft 104. The bore provides a mounting and alignment configuration for mating blade assembly 102 with arm 96.

Barrel 110 includes an inner surface (not shown) that defines a spline configuration, similar to shaft 104. The inner surface comprises splines (not shown) disposed in an axial orientation along axis A2. The splines include a plurality of individual spline members that extend in parallel relation about the circumferential inner surface. The spline configuration provides a mounting and alignment configuration, described above, for mating blade assembly 102 with arm 96.

The splines of barrel 110 mate with splines 108 along axis A2 to align and mount blade assembly 102 with arm 96 such that axis A2 intersects axis L1. The mounting and alignment configuration provides facile assembly of blade assembly 102 with arm 96. Outer surface 106 includes a flange 118 engageable to facilitate rotation of a lever 120 and arm 96. Arm 96 includes a tubular portion that is separate and rotatable relative to housing 72 via indexing lever 120 such that blade assembly 102 is rotatable about axis A2 and relative to housing 72. Lever 120 has a flip-up configuration and facilitates rotation of arm 96 upon fixation of blade assembly 102 with arm 96, as described. In an upright orientation, lever 120 can be manipulated to rotate arm 96 in the direction shown by arrows B in FIG. 3, which corresponds to rotation of retractor blades described below.

Blade assembly 102 includes a paddle and/or blade 122 for indexed rotation about axis A2 relative to housing 72 in angular increments to engage and/or distract tissue. Lever 120 rotates blade assembly 102 through an angle β and can be indexed is selected angular increments. It is envisioned that angle β may include a range of 0-85 degrees, for example, 30 degrees. It is further envisioned that the angular increments may include a range of 0-15 degrees, for example, 7.5 degrees.

Blade 122 has a substantially flat and/or substantially planar configuration and extends between a proximal end 124 and a distal end 126. Blade 122 includes a plurality of feet 128 disposed adjacent distal end 126. Feet 128 extend outwardly from distal end 126 to engage and/or distract tissue. It is envisioned that blade 122 may be oriented in alternate configurations, such as, for example, perpendicular, parallel, co-axial, angularly offset, offset and/or staggered relative to axis L1 and/or axis A2. Blade 122 is configured to retract, support and/or space tissue from the surgical site. It is contemplated that blade 122 engages tissue to separate tissue adjacent the surgical site and/or prevent tissue from entering the passageway or portal at the surgical site and/or prevent tissue creep at the surgical site. It is contemplated that blade 122 may include alternative surface configurations, which can be, for example, smooth, rough, mesh, porous, semi-porous, dimpled, arcuate, undulating, pointed and/or textured according to the requirements of a particular application.

In assembly, operation and use, surgical system 5, similar to that described, is employed, for example, with a minimally invasive surgical procedure for spinal and neurosurgical applications with a patient. For example, during spine surgery, a surgeon will make an incision in the skin of a patient's back over vertebrae to be treated. One or more dilators may be employed to gradually separate the muscles and create a portal through which the surgery may be performed.

Retractor assembly 10 is positioned adjacent the surgical site over the small incision. Blades 64, 122 are passed through the incision to create a passageway or portal to the surgical site. Blade assemblies 50, 102 are disposed at the surgical site in spaced apart relation relative to axis L1. Blade 64 is disposed along axis A1 and blade 122 is disposed along axis A2.

Blades 64, 122 may be selectively distracted and/or rotated to a selected angle about the axes, such as, for example, opening and closing to create access and/or a surgical pathway to a surgical site. For example, to open blades 64, 122 and create access and/or a surgical pathway, a practitioner engages a finger, such as, for example, a thumb with surface 30 of grip surface 24 and fingers, such as, for example, an index finger and a middle finger with finger grips 90. In one embodiment, teeth 18 of rack 16 include a one way locking configuration such that lever 86 is disposed in a non-locking configuration as shaft 12 is translated relative to housing 72 via engagement with the grip surfaces and the blades are distracted for opening, and lever 86 is disposed in a locking configuration to prevent closing of the blades. In one embodiment, the practitioner engages lever 86 for pivotable movement from the locking configuration, described above, to the non-locking configuration such that the protrusion is released from engagement with teeth 18 and shaft 12 is freely slidable relative to housing 72 to selectively position the retractor blades. It is contemplated that the practitioner may employ separate hands to engage lever 86 and the grip surfaces.

The thumb applies a force to grip surface 24 in the direction shown by arrow C in FIG. 1. The index and middle fingers apply a force to finger grips 90 in the direction shown by arrow D. The fingers together apply a compressive force to the grip surfaces in a configuration such that shaft 12 and housing 72 are drawn together to actuate shaft 12 and distract blade assemblies 50, 102. The grip surfaces are manipulated to selectively distract and/or space apart tissue at the surgical site to create access and/or a surgical pathway.

Figure 3:
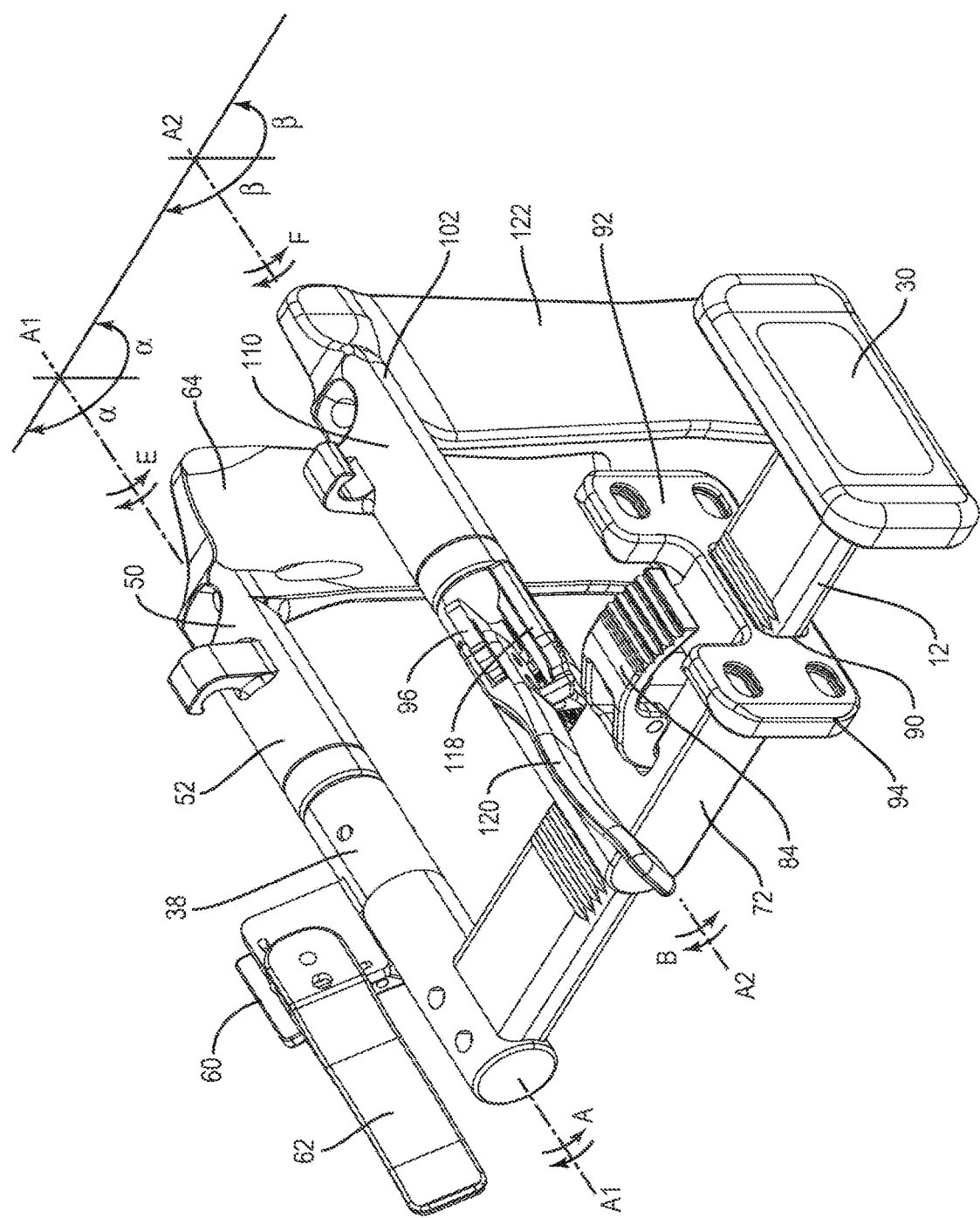
FIG. 3 is a perspective view of components of the system shown in FIG. 1.
Figure 4:
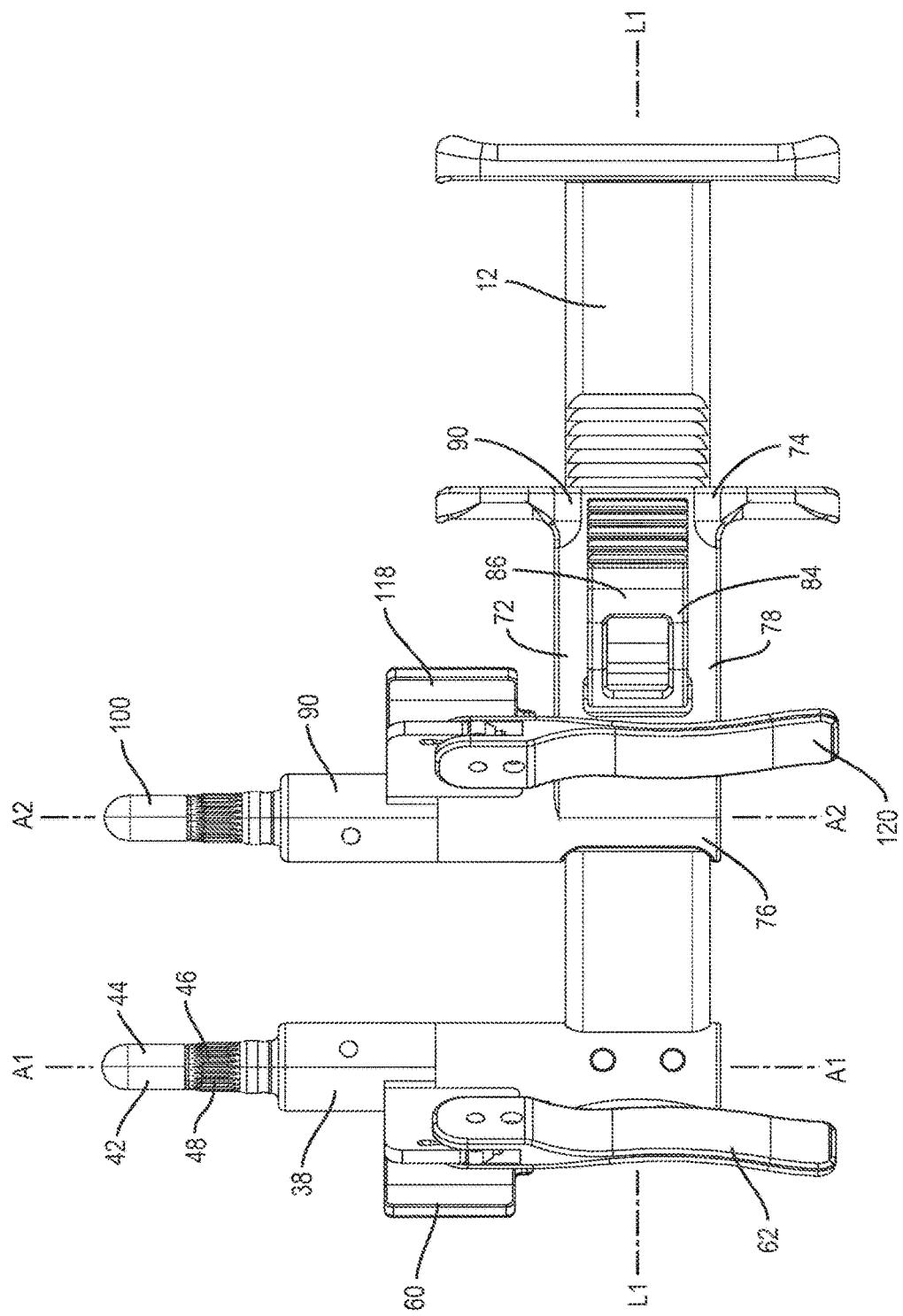
FIG. 4 is a top view of components of the system shown in FIG. 1.
Figure 5:
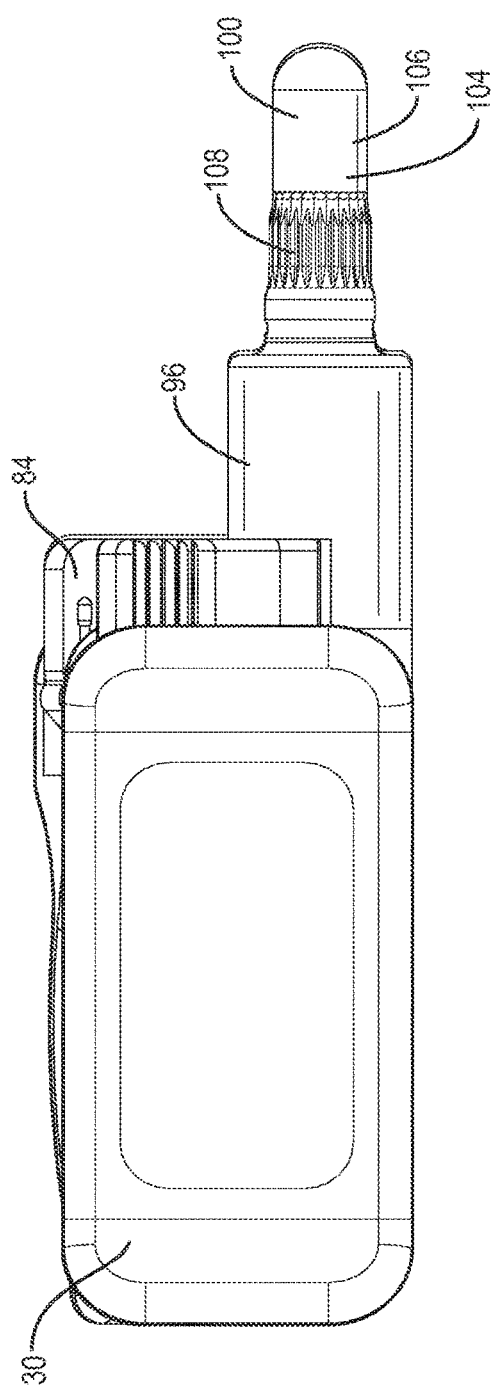
FIG. 5 is a side view of components of the system shown in FIG. 1.
Figure 6:
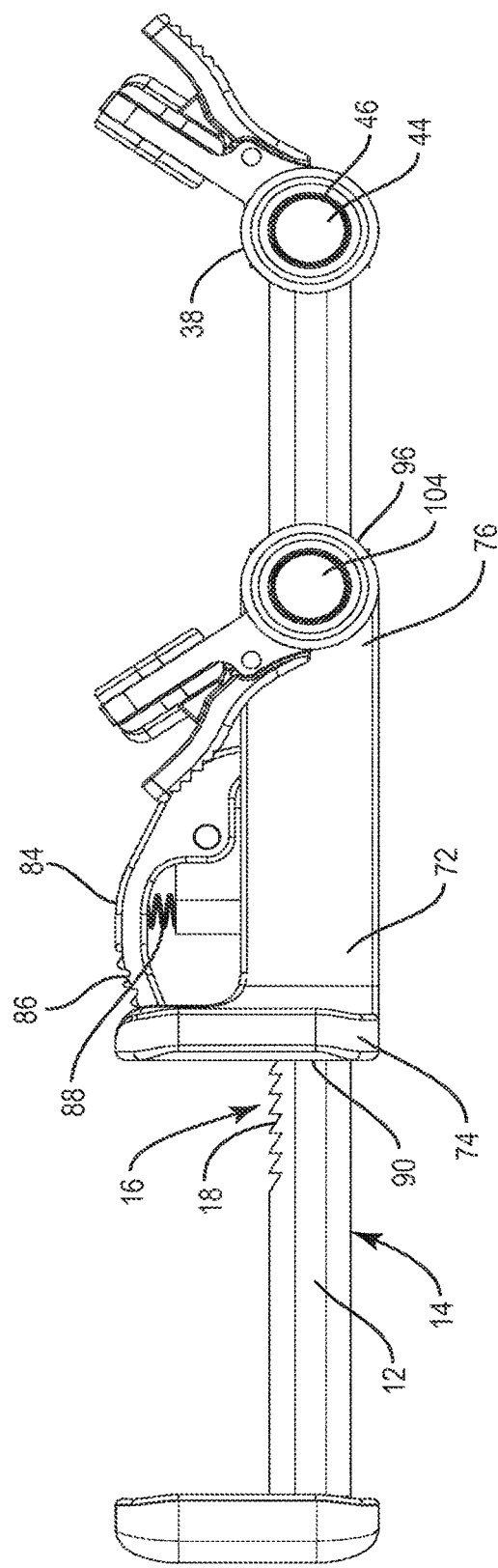
FIG. 6 is a side view of components of the system shown in FIG. 1.

Lever 62 rotates blade 64, as shown by arrows E in FIG. 3, through an angle $\alpha$ to a selected angular increment about axis A1 relative to shaft 12 to engage and/or distract tissue, according to the requirements of a particular application. Lever 120 rotates blade 122, as shown by arrows F, through an angle $\beta$ to a selected angular increment about axis A2 relative to shaft 12 to engage and/or distract tissue, according to the requirements of a particular application.

Grip surfaces 24, 90 are disposed in a configuration to conform to natural hand strength and provide tactile feedback of a 1:1 input to force ratio applied to shaft 12 and housing 72. The thumb applies a force to grip surface 24 and shaft 12 while the index and middle fingers apply counter pressure to housing 72 and finger grips 90. Blades 64, 122 engage tissue and are connected with grip surfaces 24, 90 such that grip surfaces 24, 90 provide tactile feedback of the tissue engagement to the practitioner.

Upon selected distraction of tissue, shaft 12 and housing 72 are disposed in a locking configuration such that lever 86 is released from manipulative engagement and the protrusion engages teeth 18. Shaft 12 is fixed relative to housing 72. In the locking configuration of lever 86, blades 64, 122 are selectively distracted to space apart tissue according to the requirements of a particular application. When the surgical procedure is completed, retractor assembly 10 can be unlocked and disengaged from tissue and removed.

It is envisioned that the use of microsurgical and image guided technologies may be employed to access, view and repair spinal deterioration or damage, with the aid of retractor assembly 10. It is contemplated that a surgical procedure may employ other instruments that can be mounted with retractor assembly 10, such as, for example, nerve root retractors, tissue retractors, forceps, cutter, drills, scrapers, reamers, separators, rongeurs, taps, cauterization instruments, irrigation and/or aspiration instruments, illumination instruments and/or inserter instruments.

Retractor assembly 10 may be employed for performing spinal surgeries, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 7:
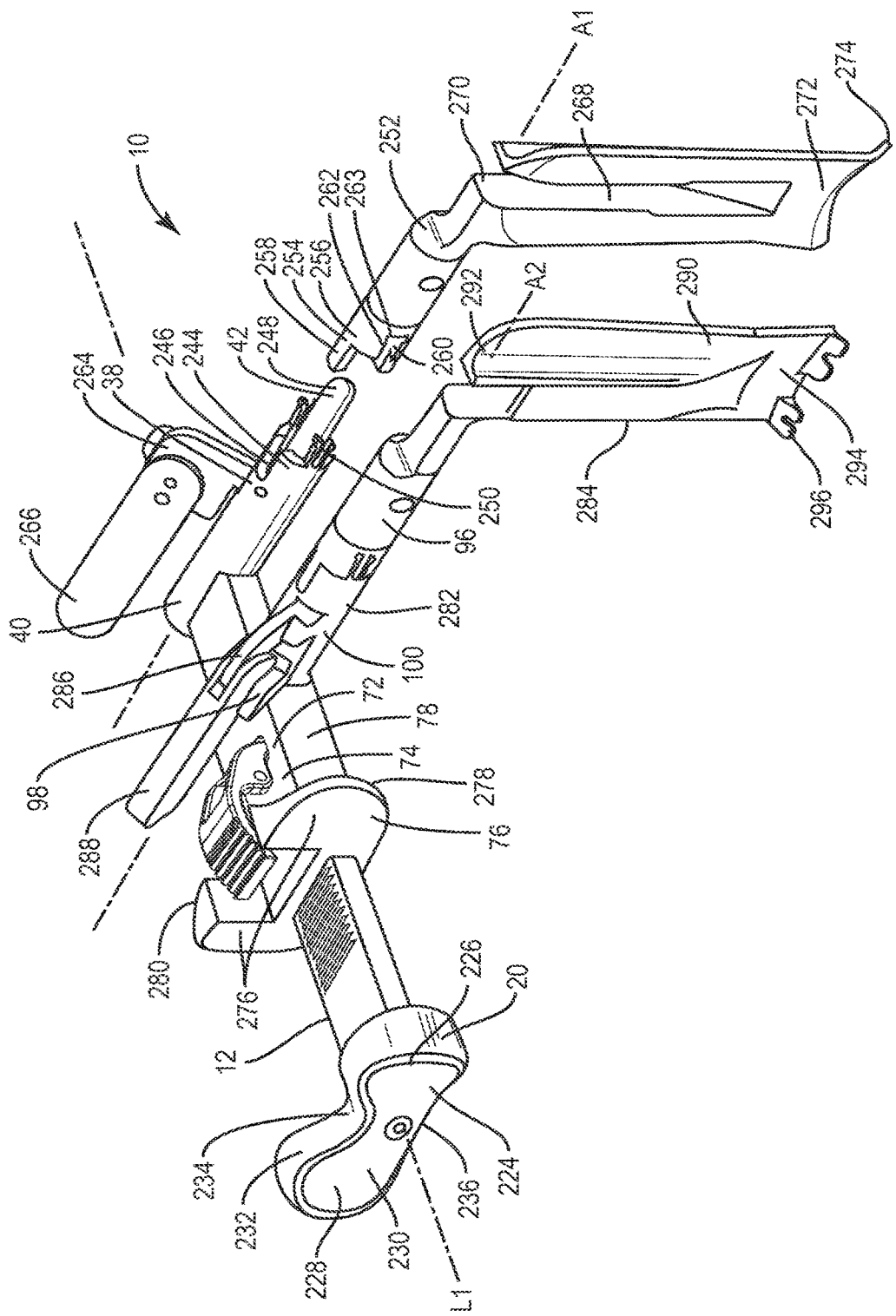
FIG. 7 is a perspective view of one embodiment of components of a system in accordance with the principles of the present disclosure.

In one embodiment, retractor assembly 10 of system 5, as shown in FIG. 7, similar to the systems and methods described above with regard to FIGS. 1-6, includes end 20 of shaft 12, as described, having a grip surface 224. Grip surface 224 includes a first portion 226 and a second portion 228. Portion 226 extends laterally outward in a first direction from outer surface 14 and transverse to axis L1. Portion 228 extends laterally outward in a second direction, opposite to the first direction of portion 226, and transverse to axis L1. It is envisioned that portion 226 and/or portion 228 may extend from outer surface 14 in various orientations, relative to axis L1, such as, for example, co-axial, angularly offset, offset and/or staggered relative to axis L1. It is contemplated that portions 226, 228 are monolithically formed with shaft 12. It is contemplated that portions 226, 228 are separate elements attached to shaft 12. It is contemplated that portions 226, 228 can be moveably connected to shaft 12.

Portions 226, 228 define a concave surface 230 that is configured for engagement with the hand of a practitioner, such as, for example, a finger, which can include a thumb. Portions 226, 228 define a continuous outer surface 232 including an undulating upper side 234 and a substantially planar lower side 236. It is contemplated that concave surface 230 includes various surface configurations, such as, for example, smooth, rough, mesh, porous, semi-porous, dimpled and/or textured according to the requirements of a particular application.

Arm 38 extends from end 40 to end 42, as described above. End 42 includes an interface configuration that mates with a first blade assembly 252. End 42 includes an outer surface 244 that defines key slots 246 disposed in opposing portions of surface 244. End 42 includes a post 248 having a detent 250. In one embodiment, detent 250 is resiliently biased for locking engagement with blade assembly 252.

Arm 38 includes blade assembly 252 for mating engagement with end 42. Blade assembly 252 includes an end 254 including an outer surface 256. Outer surface 256 defines keys 258 disposed on opposing portions of surface 256. Keys 258 are configured to fit and mate with slots 246. End 254 includes an inner surface 260 that defines a cavity 262 configured to receive and mate with post 248. Surface 256 includes a pair of recesses 263 that engage detents 250 for releasable fixation therewith.

Keys 258 engage slots 246, post 248 is disposable with cavity 262 and detents 250 to engage surface 256 such that blade assembly 252 is releasably locked with arm 38. Outer surface 246 includes a latch 264 engageable to release blade assembly 252 from arm 38. Arm 38 includes a tubular portion that is separate and rotatable relative to shaft 12 via indexing lever 266 such that blade assembly 252 is rotatable about axis A1 and relative to shaft 12, as described above.

Blade assembly 252 includes a paddle and/or blade 268 for indexed rotation about axis A1 relative to shaft 12 in angular increments to engage and/or distract tissue, similar to that described. Blade 268 has a substantially flat and/or substantially planar configuration and extends between a proximal end 270 and a distal end 272. Blade 268 includes a plurality of feet 274 disposed adjacent distal end 272. Feet 274 extend outwardly from distal end 272 to engage and/or distract tissue. It is envisioned that the blade(s) may be oriented in alternate configurations, such as, for example, perpendicular, parallel, co-axial, angularly offset, offset and/or staggered relative to axis L1 and/or axis A1. Blade 268 is configured to retract, support and/or space apart tissue from the surgical site.

End 76 of housing 74 includes finger grips 276, similar to grips 90 described above. Finger grips 276 include a first portion 278 and a second portion 280. Portion 278 extends laterally from outer surface 78. Portion 278 is configured for engagement with a hand of a practitioner, such as, for example, a first finger. Portion 280 extends laterally from outer surface 78 in an opposite direction from portion 278. Portion 280 is configured for engagement with a hand of a practitioner, such as, for example, a second finger.

Arm 96, described above, extends from end 98 to end 100. End 100 includes outer surface 282 and a blade interface configuration that mates with blade assembly 284. Arm 96 includes blade assembly 284 for mating engagement with end 100, similar to blade assembly 252. Outer surface 282 includes a latch 286 engageable to release blade assembly 284 from arm 96. Arm 96 includes a tubular portion that is separate and rotatable relative to housing 72 via indexing lever 288 such that blade assembly 284 is rotatable about axis A2 and relative to housing 72. Blade assembly 284 includes a paddle and/or blade 290 for indexed rotation about axis A2 relative to housing 72 in angular increments to engage and/or distract tissue.

Blade 290 has a substantially flat and/or substantially planar configuration and extends between a proximal end 292 and a distal end 294. Blade 290 includes a plurality of feet 296 disposed adjacent distal end 294. Feet 296 extend outwardly from distal end 294 to engage and/or distract tissue.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical retractor comprising:
   a first member including a shaft, the shaft comprising opposite first and second ends, the first member comprising a first grip coupled to the first end and a first blade coupled to the second end; and
   a second member including a housing comprising opposite first and second ends, the second member comprising a second grip coupled to the first end of the housing such that the second grip extends outwardly from opposite sides of the housing, the second member comprising a second blade coupled to the second end of the housing, the second member comprising a passageway,
   wherein the shaft is positioned in the passageway such that the second grip and the second blade are positioned between the first grip and the first blade, and
   wherein the grips are configured to be drawn together to move the first blade away from the second blade.

2. The surgical retractor recited in claim 1, wherein the retractor is configured to be operated manually and is free of any electrical components and is not in communication with any electrical components.

3. The surgical retractor recited in claim 1, wherein the first grip has a maximum height that is greater than a maximum height of the housing and a maximum width that is greater than a maximum width of the housing.

4. The surgical retractor recited in claim 1, wherein the first member comprises an arm having opposite first and second ends, the first end of the arm being coupled directly to the second end of the shaft, the second end of the arm being coupled directly to the first blade, the first end of the arm and the first grip each having a maximum height that is greater than a maximum height of the passageway.

5. The surgical retractor recited in claim 1, wherein the first grip has a maximum height that is greater than a maximum height of the passageway and a maximum width that is greater than a maximum width of the passageway.

6. The surgical retractor recited in claim 1, wherein the first member comprises an arm having opposite first and second ends, the first end of the arm being coupled directly to the second end of the shaft, the second end of the arm being coupled directly to the first blade, the first end of the arm and the first grip each having a maximum height that is greater than a maximum height of the passageway and a maximum width that is greater than a maximum width of the passageway.

7. The surgical retractor recited in claim 1, wherein the first grip has a maximum height that is substantially equal to a maximum height of the second grip and a maximum width that is substantially equal to a maximum width of the second grip.

8. The surgical retractor recited in claim 1, wherein the first grip has a maximum height that is equal to a maximum height of the second grip and a maximum width that is equal to a maximum width of the second grip.

9. The surgical retractor recited in claim 1, wherein the second grip has a first portion, a second portion and a gap between the first portion and the second portion, the first portion and the second portion each comprising spaced apart holes, the holes each extending parallel to the passageway.

10. The surgical retractor recited in claim 1, wherein the second grip has a first portion, a second portion and a gap between the first portion and the second portion, the second member comprising a lock rotatably coupled to the housing, the lock being configured to engage the shaft, a portion of the lock being positioned in the gap.

11. The surgical retractor recited in claim 1, wherein the shaft comprises a plurality of teeth, the second member comprising a lock rotatably coupled to the housing, the lock being configured to engage the teeth to prevent movement of the shaft relative to the housing.

12. The surgical retractor recited in claim 1, wherein:
the first member comprises a first arm having opposite first and second ends, the first end of the first arm being coupled directly to the second end of the shaft, the second end of the first arm being coupled directly to the first blade, the second member comprising, a second arm having opposite first and second ends, the first end of the second arm being coupled directly to the second end of the housing, the second end of the second arm being coupled directly to the second blade; and
the first arm extends parallel to the second arm as the first blade moves away from the second blade.

13. The surgical retractor recited in claim 1, wherein the first member comprises a first arm having opposite first and second ends, the second end of the first arm being rotatable relative to the first end of the first arm, the first end of the first arm being fixed directly to the second end of the shaft, the second end of the first arm being coupled directly to the first blade, the second member comprising a second arm having opposite first and second ends, the second end of the second arm being rotatable relative to the first end of the second arm, the first end of the second arm being fixed directly to the second end of the housing, the second end of the second arm being coupled directly to the second blade.

14. The surgical retractor recited in claim 13, wherein:
the first end of the first arm includes a first shaft that is disposed in a first socket of the second of the first arm; and
the first end of the second arm includes a second shaft that is disposed in a second socket of the second end the second arm.

15. The surgical retractor recited in claim 13, wherein:
the first end of the first arm includes a first shaft that is disposed in a first socket of the second of the first arm such that splines of the first shaft engage splines of the first socket; and
the first end of the second arm includes a second shaft that is disposed in a second socket of the second end the second arm such that splines of the second shaft engage splines of the second socket.

16. The surgical retractor recited in claim 1, wherein the first grip is permanently fixed to the first end of the shaft and the second grip is permanently fixed to the first end of the housing.

17. The surgical retractor recited in claim 1, wherein the second grip includes a surface configured to engage a surface of the first grip, the passageway extending through the surface of the second grip.

18. The surgical retractor recited in claim 1, wherein the shaft is configured to translate relative to the housing in a first direction to move the first blade away from the second blade and in an opposite second direction to move the first grip away from the second grip to move the first blade toward the second blade, the shaft being configured to translate relative to the housing in the first direction until the first grip directly engages the second grip.

19. A surgical retractor comprising:
a first member including a shaft, the shaft comprising opposite first and second ends, the first member comprising a first grip permanently fixed to the first end and a first blade coupled to the second end; and
a second member including a housing comprising opposite first and second ends, the second member comprising a second grip permanently fixed to the first end of the housing and a second blade coupled to the second end of the housing, the second member comprising a passageway,
wherein the shaft is positioned in the passageway such that the second grip and the second blade are positioned between the first grip and the first blade,
wherein the first member comprises an arm having opposite first and second ends, the first end of the arm being coupled directly to the second end of the shaft, the second end of the arm being coupled directly to the first blade, the first end of the arm and the first grip each having a maximum height that is greater than a maximum height of the passageway and a maximum width that is greater than a maximum width of the passageway,
wherein the shaft is configured to translate relative to the housing in a first direction to move the first blade away from the second blade and in an opposite second direction to move the first grip away from the second grip to move the first blade toward the second blade, the shaft being configured to translate relative to the housing in the first direction until the first grip directly engages the second grip, and
wherein the retractor is configured to be operated manually and is free of any electrical components and is not in communication with any electrical components.

20. A surgical retractor comprising:
a first member including a shaft, the shaft comprising opposite first and second ends, the first member comprising a first grip permanently fixed to the first end and a first blade coupled to the second end; and
a second member including a housing comprising opposite first and second ends, the second member comprising a second grip permanently fixed to the first end of the housing and a second blade coupled to the second end of the housing, the second member comprising a passageway,
wherein the shaft is positioned in the passageway such that the second grip and the second blade are positioned between the first grip and the first blade,
wherein the second grip has a first portion, a second portion and a gap between the first portion and the second portion, the second member comprising a lock rotatably coupled to the housing, the lock being configured to engage teeth of the shaft to prevent movement of the shaft relative to the housing, the lock being positioned in the gap,
wherein the first member comprises an arm having opposite first and second ends, the first end of the arm being coupled directly to the second end of the shaft, the second end of the arm being coupled directly to the first blade, the first end of the arm and the first grip each having a maximum height that is greater than a maximum height of the passageway and a maximum width that is greater than a maximum width of the passageway, wherein the shaft is configured to translate relative to the housing in a first direction to move the first blade away from the second blade and in an opposite second direction to move the first grip away from the second grip to move the first blade toward the second blade, the shaft being configured to translate relative to the housing in the first direction until the first grip directly engages the second grip, and wherein the retractor is configured to be operated manually and is free of any electrical components and is not in communication with any electrical components.

\* \* \* \* \*